United States Patent [19]

Dolfini et al.

[11] Patent Number: 4,927,805

[45] Date of Patent: May 22, 1990

[54] HYDROLYSIS OF CURCUMIN

[75] Inventors: Joseph E. Dolfini; Jerome Glinka, both of Cincinnati; Andrew C. Bosch, Mason, all of Ohio

[73] Assignee: Mallinckrodt, Inc., St. Louis, Mo.

[21] Appl. No.: 301,873

[22] Filed: Jan. 25, 1989

Related U.S. Application Data

[63] Continuation-in-part of Ser. No. 123,137, Nov. 20, 1987, Pat. No. 4,810,824, which is a continuation-in-part of Ser. No. 10,902, Feb. 4, 1987, Pat. No. 4,709,098.

[51] Int. Cl.$^5$ .................... A61K 7/46; C07C 47/575; C07C 47/58
[52] U.S. Cl. ............................... 512/27; 512/8; 512/25; 512/26; 568/425; 568/426; 568/491
[58] Field of Search ............... 568/425, 426, 491; 512/8, 20, 25, 26, 27

[56] References Cited

U.S. PATENT DOCUMENTS

| | | | |
|---|---|---|---|
| 4,617,419 | 10/1986 | Wiener et al. | 568/464 |
| 4,709,098 | 11/1987 | Dolfini et al. | 568/491 |
| 4,727,058 | 2/1988 | Pittet et al. | 512/21 |

FOREIGN PATENT DOCUMENTS

| | | | |
|---|---|---|---|
| 505952 | 9/1954 | Canada | 568/426 |
| 875512 | 3/1953 | Fed. Rep. of Germany | 568/491 |
| 927688 | 5/1955 | Fed. Rep. of Germany | 568/3 |
| 946443 | 8/1956 | Fed. Rep. of Germany . | |
| 2219455 | 11/1972 | Fed. Rep. of Germany | 568/426 |
| 2459791 | 1/1981 | France . | |
| 1519093 | 7/1978 | United Kingdom . | |

OTHER PUBLICATIONS

Annalen, vol. 289, p. 337, (w/translation).
Chemical Abstracts 91:192978y.

*Primary Examiner*—Werren B. Lone
*Attorney, Agent, or Firm*—Wood, Herron & Evans

[57] ABSTRACT

Curcumin is subjected to the action of heat and pressure in the presence of water by a continuous or batch process to produce vanillin and other natural flavor products. The proportion of vanillin in the final product varies with the pH of the reaction mixture.

18 Claims, No Drawings

HYDROLYSIS OF CURCUMIN

RELATED APPLICATION

This is a continuation-in-part of application Ser. No. 07/123,137, filed Nov. 10, 1987, U.S. Pat. No. 4,810,824, which is a continuation-in-part of application Ser. No. 10,902, filed Feb. 4, 1987, and issued as U.S. Pat. No. 4,709,098, invented by Joseph E. Dolfini and Jerome Glinka, and assigned to the assignee of this application.

BACKGROUND OF THE INVENTION

In the field of organic chemistry, reaction products different in form from their starting materials can be obtained by means of a large number of reaction sequences. Organic starting materials particularly amenable to reaction are alkene compounds, otherwise known as olefins. Olefins are characterized by the presence of one or more carbon-carbon double bonds. Reactions involving olefins usually occur at the carbon-carbon double bonds. The double bond can be eliminated by addition of atoms to the olefin molecule. The double bond can also be shifted from one carbon-carbon couple to another within the molecule. The double bond can also be cleaved to form two or more smaller molecules from one olefin molecule having one or more double bonds. Cleavage is accomplished by a small number of reaction sequences such as ozonolysis, oxidation and the like. Generally, cleavage occurs by the addition of oxygen to the double bond carbons which then destroys the bond between the carbons.

The presence of a substituent group on the olefin compound sometimes permits the double bond to be broken under less vigorous conditions. One such substituent is the carbonyl group, which consists of a carbon doubly bonded to oxygen. A carbonyl group having its double bond conjugated with the olefin double bond can activate the olefin double bond and cause it to break in the presence of alkaline catalyst, heat and water. This reaction is known as a reverse or retro-aldol condensation which is subject to side reactions and reaction product condensations. In the presence of only heat and water, typically no reaction occurs.

One reference has been found which describes the cleavage of a substituted conjugated cyclohexanone molecule in the presence of heat, pressure and water without any added alkaline catalyst. The reaction as cited in *Annalen*, Vol. 289, p. 337 (1896), involved the formation of acetone and 3-methyl-cyclohexanone in an autoclave at 250° C. from pulegone and water. It is believed that pulegone underwent reaction under the above conditions because the position of the substituents on the cyclohexyl ring caused a destabilization of the olefin, permitting reaction to occur.

German Patent No. 875512 to Binapfl discloses a procedure for splitting certain unsaturated ketones having the carbonyl double bond conjugated with the carbon-carbon double bond. Splitting occurred when the ketone was heated in the presence of water, preferably with added acid. The hydrogen atom in the water molecule was directed to the carbon atom of the double bond closest to the carbonyl group, with oxygen being directed to the remaining carbon of the double bond, thereby forming a product ketone or aldehyde. For example, a mixture of cyclohexylidenecyclohexanone-2 and water was heated to a temperature of about 295° C. to 300° C. in a pressure vessel to yield cyclohexanone.

SUMMARY OF THE INVENTION

As reported in our related U.S. Pat. No. 4,709,098 to Dolfini et al, the hydrolysis of acyclic olefins having an aldehyde or ketone radical substituent conjugated with the carbon-carbon double bond of the olefin proceeds in the presence of water at a substantially neutral pH at a temperature in the range of about 200° to about 300° and under pressure in the range of about 225 to about 1250 psi. For example, cinnamaldehyde was heated to about 250° C. in the presence of water at about 680 psi to produce benzaldehyde. It was also disclosed in our related U.S. application Ser. No. 07/123,137, filed Nov. 20, 1987 that the diketone compound curcumin, i.e., 1,7-bis(4-hydroxy-3-methoxy-phenyl)-1,6-heptadiene-3,5-dione, may be hydrolyzed to produce vanillin, and that the hydrolysis reaction can be effectively conducted at even higher temperatures and pressures of up to about 325° C. and about 2000 psi. It was found that curcumin may be hydrolyzed in the presence of heat, pressure and water to break the conjugated carbon-carbon double bonds and form the carbonyl-containing compound vanillin, 4-hydroxy-3-methoxybenzaldehyde, which finds substantial use as a flavor compound. The hydrolysis reaction causes cleavage of a substantial portion of the curcumin to provide very practical yields.

The hydrolysis of curcumin to produce vanillin as practiced by this invention is believed to proceed in the presence of heat, pressure and water. Presumably, if acid or base is used to initiate the hydrolysis reaction, other flavor reaction products may be obtained. One of the advantages of this invention is the production of natural flavors from natural sources simply under the reaction conditions of temperature, pressure, and water with no catalysts.

It has been found that the action of heat, pressure and water on the diketone curcumin causes formation of hitherto unexpected compounds such as guaiacol, vinyl guaiacol, vanillylidene acetone and ferulic acid, in addition to vanillin. However, the relative proportion of the flavor compounds varies with the presence of acid or base in the reaction mixture. With the addition of base, guaiacol may be the principal reaction product, for example. Also, the relative proportion of flavor compounds can vary by altering the time and temperature parameters of the reaction.

In another of its features, according to this invention, substantially all curcumin is obtained by solvent extracting turmeric spice, derived from the turmeric root. The solvents employed typically are acetone, ethylene dichloride or ethyl acetate. The crude extract is then further washed with organic solvents such as hexane, cold ethylene dichloride, pentane or petroleum ether to remove organic impurities, thereby producing a dry powder concentrated to about 95% by weight curcumin. The naturally-derived curcumin is also known in commerce as turmeric oleoresin powder.

The method of reaction claimed herein is preferably carried out in a continuous flow reactor, such as a tube reactor. However, the hydrolysis reaction may be successfully accomplished in an autoclave or other batch-type apparatus. The water may be distilled or deionized, but tap water is also sufficient. Typically, a molar excess of water relative to curcumin is employed.

Because of the nature of the reaction, non-reactive species present in the starting material will have little effect on the cleavage of the reactive bonds in curcumin. As a result, the natural sourcing of curcumin has no adverse effect on the formation of desirable flavor products in substantial yield.

Without holding applicant to a specific theory, it is believed that, in addition to hydrolysis of curcumin to produce vanillin, the competing fragmentation reaction of acetone derivative formation occurs to produce compounds other than vanillin. Thus, in the presence of heat, pressure and water, a portion of curcumin is believed to fragment to form vanillylidene acetone [4-(p-hydroxy-m-methoxyphenyl)2-butenone] and ferulic acid [3-(4-hydroxy-3-methoxy-phenyl)-2-propenoic acid], instead of forming vanillin. The vanillylidene acetone further hydrolyzes at a moderate rate to produce vanillin and acetone. Ferulic acid rapidly decarbonylates to form vinyl guaiacol and carbon dioxide. The vinyl guaiacol itself may further dealkylate to produce guaiacol. Further, vanillin itself decarbonylates to form guaiacol and carbon monoxide.

The overall product proportions are found to vary with pH of the reaction mixture. Formation of vanillin is maximized by permitting the pH to drop naturally during the hydrolysis reaction of curcumin. From an essentially neutral pH at the point of mixing of curcumin, water and preferably a cosolvent, such as diglyme, the pH of the mixture is allowed to drop due to formation of acidic products during the reaction procedure. Typically, the pH will drop to a value within the range of about 4.0 to 4.2 when the reaction is conducted in an autoclave. The final pH of the reaction mixture in a continuous reactor will typically be slightly higher. Below a pH of 4, vanillin production essentially ceases. Where the pH of the reaction mixture was maintained at about 7 using a buffer, or was allowed to become alkaline, vanillin formation decreased and production of guaiacol increased.

DETAILED DESCRIPTION

The method in its broader aspects is practiced by reacting curcumin by hydrolyzing with heating in the pressure of water to effect the reaction and thereby produce a flavor compound. More specifically, the method is practiced by conducting the reaction of curcumin at a temperature in the range of about 200° to about 325° C. and at a pressure of about 225 to about 2000 psi sufficient to produce vanillin. At temperatures substantially below about 200° C., the reaction rate is too slow to permit economical production of flavor compounds. At temperatures substantially above about 325° C., the flavor compounds tend to decompose. The pH of the reaction can be controlled to produce certain flavor compounds in certain proportions. It is also known that the relative proportion of flavor compounds in the reaction product can be altered by varying the time and temperature parameters of the reaction. The flavor compounds are selected varying from the group consisting of vanillin, vanillylidene acetone, guaiacol, vinyl guaiacol, and mixtures thereof. Substantially all curcumin in commerce is obtained from the natural turmeric root, and is more specifically an extract from the turmeric spice. Curcumin is also known as turmeric oleoresin.

It is preferred that the reaction of curcumin with water be carried out in the presence of a cosolvent, such as diglyme. Also, it is preferred that the reaction of curcumin be carried out in a continuous reactor to realize increased production of reaction product on an economical basis.

To form a natural flavor product having excellent properties the natural material turmeric oleoresin containing about 95% by weight curcumin is combined with water and diglyme cosolvent, the water being at a substantially neutral pH, and heating at a temperature of about 200° to about 325° C. at a pressure of about 225 to about 2000 psi with a consequent decrease of pH to produce the natural flavor product. Vanillin production is maximized if the pH is allowed to drop from a substantially neutral value to no less than about 4. The natural flavor product contains, as primary components, vanillin, followed by guaiacol, vanillylidene acetone and vinyl guaiacol. Again, production is preferably carried out in a continuous reactor.

The invention is also intended to encompass the products produced by the process involving curcumin and the natural source thereof, i.e., turmeric oleoresin. The components formed in addition to vanillin contribute to the overall flavor characteristics of the natural flavor product. Thus, when starting with turmeric oleoresin, the combination natural flavor product comprising vanillin, guaiacol and vinyl guaiacol, among other components is unique to the process of hydrolyzing the oleoresin starting material.

OPERATING EXAMPLES

The following detailed operating examples illustrate the practice of the invention in its most preferred form, thereby enabling a person of ordinary skill in the art to practice the invention. The principles of this invention, its operating parameters and other obvious modifications thereof will be understood in view of the following detailed procedure.

EXAMPLE I

About 2000 grams of stirred suspension of 1% turmeric oleoresin, 95.5% water, and 3.5% diglyme [bis(2-methoxyethyl)ether] was prepared. This suspension was then pumped into a reaction tube heated to 316° C. and pressurized to 1680 psi valved to permit continuous feed and recovery of product. The flow rate through the tube is set to give a residence time of about 30 minutes. The effluent from the tube was cooled and extracted with ethyl acetate. The effluent had a pH of about 4.8. The recovered natural flavor products were 20% vanillin, 12% guaiacol, 9% vanillylidene acetone, and 5% vinyl guaiacol, based upon the initial charge of oleoresin. The remainder was comprised of non-volatile resinous materials and minor amounts of phenol and zingerone.

EXAMPLE II

To demonstrate the effect of pH on the final natural product composition, 10 g of turmeric oleoresin was charged into a 600 ml Parr autoclave with 360g of a sodium acetate buffer solution at pH 7. The mixture was heated to 250° C. for 2 hours at a final pressure of about 560 psi. After cooling, the organic phase was extracted with ethyl acetate and analyzed. The resultant natural product blend was comprised of 20% guaiacol based on the initial charge of oleoresin. The remainder was non-volatile resinous materials. The final pH of the solution was 6.2.

By following the teachings of this invention, it can be seen that natural vanillin can be formed by treating curcumin under the conditions envisioned by the method of this invention. Further, the presence of flavor products in addition to vanillin modifies the flavor of the vanillin to produce a flavor having unique organoleptic properties. By modifying the pH of the reaction solution, the relative amounts of the flavor product components can be altered, thereby permitting formation of flavor products having a range of organoleptic properties.

Having described this invention, and its operating parameters, variations may be achieved without departing from the spirit and scope hereof.

What is claimed is:

1. A method of reacting curcumin with water to produce a flavor compound comprising at least one reaction product of curcumin and water, comprising:
hydrolyzing with heating curcumin in the presence of water at a temperature and pressure sufficient to effect the reaction and thereby produce said compound.

2. The method of claim 1 wherein said reaction is conducted at a temperature of about 200° to about 325° C. and at a pressure of about 225 to about 2000 psi sufficient to produce vanillin.

3. The method of claim 1 wherein the pH of said reaction is controlled to produce a flavor compound.

4. The method of claim 3 wherein said flavor compound is selected from the group consisting of vanillin, vanillylidene acetone, guaiacol, vinyl guaiacol, and mixtures thereof.

5. The method of claim 1 wherein said curcumin is an extract from the turmeric spice.

6. The method of claim 1 wherein said reaction is conducted in the presence of said water and a co-solvent.

7. The method of claim 6 wherein said cosolvent is diglyme.

8. The method of claim 1 conducted in a continuous reactor.

9. The product produced from the method of claim 1.

10. The product produced from the method of claim 4.

11. A method of forming a natural flavor product from turmeric oleoresin and water containing at least one reaction product of turmeric oleoresin and water, comprising:
mixing said oleoresin with water and hydrolyzing with heating at a temperature and pressure sufficient to produce said natural flavor product.

12. The method of claim 11, wherein said hydrolyzing is conducted at a temperature of about 200° to about 325° C. and a pressure of about 225 to about 2000 psi to produce vanillin.

13. The method of claim 11 wherein the pH of said reaction is controlled to produce a flavor compound.

14. The method of claim 12 wherein pH is initially substantially neutral and subsequently decreases as said reaction proceeds.

15. The method of claim 14 wherein said pH is not less than about 4.

16. The method of claim 13 wherein said natural flavor product is selected from the group consisting of vanillin, vanillylidene acetone, guaiacol, vinyl guaiacol and mixtures thereof.

17. The method of claim 11 conducted in a continuous reactor.

18. The product produced from the method of claim 16.

* * * * *

UNITED STATES PATENT AND TRADEMARK OFFICE
CERTIFICATE OF CORRECTION

PATENT NO. : 4,927,805
DATED : May 22, 1990
INVENTOR(S) : Joseph E. Dolfini et al It is certified that error appears in the above-identified patent and that said Letters Patent is hereby corrected as shown below:

Column 1, lines 1 and 2 "HYDROLYSIS OF CURCUMINcl RELATED APPLICATION"

should be --HYDROLYSIS OF CURCUMIN RELATED APPLICATION--

Column 1, line 6 "November 10" should be --November 20--

Column 3, line 11 "methoxyphenyl)2-butenone] should be --methoxyphenyl)-2-butenone]--

Signed and Sealed this

Fourth Day of February, 1992

Attest:

HARRY F. MANBECK, JR.

*Attesting Officer*     *Commissioner of Patents and Trademarks*